United States Patent [19] [11] 4,325,951
Inouye et al. [45] Apr. 20, 1982

[54] 1-OXADETHIACEPHALOSPORIN DERIVATIVES AND ANTIBACTERIAL USE THEREOF

[75] Inventors: Shigeharu Inouye, Yokohama; Takashi Tsuruoka, Kawasaki; Katsuyoshi Iwamatsu, Yokohama, all of Japan

[73] Assignee: Meiji Seika Kaisha, Ltd., Tokyo, Japan

[21] Appl. No.: 200,410

[22] Filed: Oct. 24, 1980

[30] Foreign Application Priority Data
Nov. 2, 1979 [JP] Japan .................. 54-141297

[51] Int. Cl.$^3$ .................. A61K 31/535; C07D 498/04
[52] U.S. Cl. .................. 424/248.52; 544/90
[58] Field of Search .................. 544/90; 424/248.52

[56] References Cited
U.S. PATENT DOCUMENTS 4,138,486  2/1979  Narisada et al. .................. 424/248.52
4,226,864 10/1980  Narisada et al. .................. 544/90 X
4,226,866 10/1980  Christensen et al. .................. 544/90 X
4,232,151 11/1980  Nagata et al. .................. 544/90

Primary Examiner—Richard Raymond
Attorney, Agent, or Firm—Larson and Taylor

[57] ABSTRACT

New antibacterial 1-oxadethiacephalosporin derivatives of the general formula

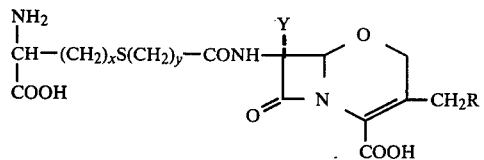

wherein R is a heterocyclic group or a group —S—Het where Het denotes a heterocyclic group, Y is a hydrogen atom or a methoxy group; x and y are each an integer of 1 to 3 is produced by a process comprising condensing a 1-oxacephem compound of the formula

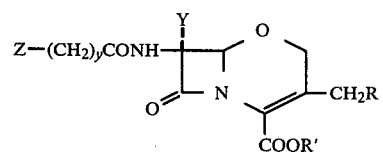

wherein R, Y, y are as defined above; R' is a hydrogen atom or a carboxyl-protecting group; and Z is a halo group, with a sulfur-containing amino acid of the formula

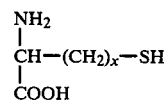

wherein x is as defined above, in a solvent and removing, if necessary, the residual protective group from the resultant condensation product. The new 1-oxadethiacephalosporin derivatives and the pharmaceutically acceptable salts and esters thereof exhibit high and broad "in vitro" and "in vivo" antibacterial activity, particularly against β-lactamase-producing strains of gram-negative bacteria.

10 Claims, No Drawings

1-OXADETHIACEPHALOSPORIN DERIVATIVES AND ANTIBACTERIAL USE THEREOF

BACKGROUND OF THE INVENTION

1. Field of the Invention

This invention relates to new, antibacterial 1-oxadethiacephalosporin derivatives exhibiting high "in vitro" and "in vivo" antibacterial activity, particularly against the $\beta$-lactamase-producing bacteria. This invention also relates to a process for the production of the new 1-oxadethiacepharosporin derivatives. This invention further relates to antibacterial composition containing said 1-oxadethiacephalosporin derivatives as well as to the chemotherapeutic use of these 1-oxadethiacephalosporins and the pharmaceutically acceptable salts and esters thereof.

2. Description of the Prior Art

Many, various derivatives of cephalosporin have been produced and used in therapeutic treatment of bacterial infections. In the recent years, various derivatives of 1-oxadethiacephalosporin have been produced synthetically and proposed to be used for in therapeutic treatment of bacterial infections (see, for example, U.S. Pat. Nos. 4,011,216; 4,013,648; 4,013,653; 4,031,083; 4,045,438; 4,138,486 and 4,180,571). We have researched extensively in an attempt to provide new further derivatives of 1-oxadethiacephalosporin having high and broad antibacterial activity against gram-positive and gram-negative bacteria and even against the $\beta$-lactamase-producing strains which are usually resistant to the known cephalosporins. As a result of our studies, we have now succeeded to synthetize new derivatives of 1-oxadethiacephalosporin, and we have found that these new derivatives of 1-oxadethiacephalosporin now synthetized have more excellent antibacterial properties than those of the known cephalosporin derivatives.

SUMMARY OF THE INVENTION

An object of this invention is to provide new derivatives of 1-oxadethiacephalosporin which exhibit high antibacterial activity and are useful in chemotherapeutic treatment of bacterial infections. The other object of this invention is to provide a process for the production of the above new compound which can be carried out in an efficient and facile way and is suitable for commercial production of the new compound. Further object of this invention will be clear from the following descriptions.

According to a first aspect of this invention, therefore, there are provided a new 1-oxadethiacephalosporin derivative of the general formula (I):

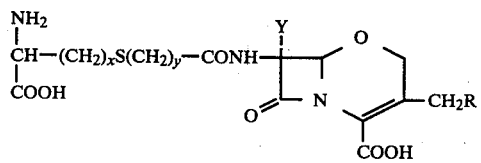

wherein R is a heterocyclic group or a group —S—Het where Het denotes a heterocyclic group, Y is a hydrogen atom or a methoxy group —OCH$_3$, and x and y each denote an integer of 1, 2 or 3, and pharmaceutically acceptable salts and esters thereof.

According to a second aspect of this invention, there is provided a process for the production of the new 1-oxadethiacephalosporin derivative of the general formula (I) shown above, which comprises the steps of:

(a) condensing a 1-oxacephem compound of the formula (II):

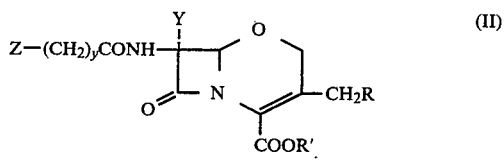

wherein R is a heterocyclic group or a group —S—Het where Het denotes a heterocyclic group, Y is a hydrogen atom or a methoxy group —OCH$_3$, R' is a hydrogen atom or a carboxyl-protecting group, particularly an ester-forming group known as the carboxyl-protecting group, Z is a halo group, especially bromo, chloro or iodo, y denotes an integer of 1, 2 or 3, with a sulfur-containing amino acid of the formula (III):

wherein x denotes an integer of 1, 2 or 3 or a functionally equivalent derivative of said amino acid, in a solvent to produce the condensation product of the formula (I'):

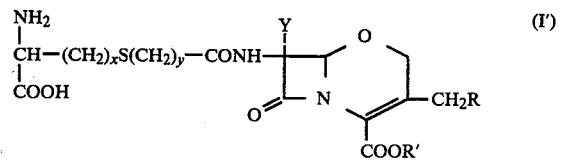

wherein R, R', Y, x and y are as defined above, and (b) removing, if necessary, the residual protecting group from the condensation product (I') in a known manner, when such residual protecting group is present.

DETAILED DESCRIPTION OF THE INVENTION

The 1-oxadethiacephalosporin derivative of the formula (I) according to the first aspect of this invention may also be in the form of its pharmaceutically acceptable salt with an alkali metal such as sodium and potassium, or with a basic amino acid such as L-lysine or with a pharmaceutically acceptable organic base such as triethylamine and cyclohexylamine. Furthermore, the 1-oxadethiacephalosporin derivative of the formula (I) may be in the form of its pharmaceutically acceptable ester (as the carboxylate) with a pharmaceutically acceptable alcohol. The ester may be present as a lower (C$_1$-C$_6$) alkyl ester such as methyl, ethyl, propyl or t-butyl ester; and alkylamino-lower alkyl ester such as dimethylaminoethyl ester; an alkoxy-lower alkyl ester such as methoxymethyl, ethoxyethyl or ethoxyethyl ester; an acyloxy-lower alkyl ester such as acetoxymethyl, acetoxyethyl, propionyloxymethyl, propionyloxyethyl, pivaloyloxymethyl, pivaloyloxyethyl ester; and an alkoxycarbonyloxy-lower alkyl ester such as methoxycarbonyloxymethyl, methoxycarbonyloxyethyl, ethoxycarbonyloxymethyl or ethoxycarbonyloxyethyl ester, and the like. The ester may preferably be the phthalidyl, acetoxymethyl, pivaloyloxymethyl, acetoxyethyl, propionyloxyethyl, indanyl, phenyl dimethylphenyl, methoxyphenyl, methoxycarbonyloxyethyl, ethoxycarbonylmethyl or phenacyl ester. Besides, the ester may be either in the form of the mono-ester at the 4-carboxyl group of the 1-oxacephem nucleus or at the terminal carboxyl substituent present in the amino acid moiety attaching to the 7-amino group of the 1-oxacephem nucleus, or in the form of the di-ester at these two carboxyl groups.

The amino acid moiety attaching to the 7-amino group of the 1-oxacephem nucleus present in the molecule of the new compound of the formula (I) may be in the form of either the D-stereoisomer or the L-stereoisomer within the concept of this invention. The D-form usually exhibit a higher antibacterial activity than the L-form. The compound of the formula (I) where Y is the methoxy group —OCH$_3$ exhibits an antibacterial activity as high as that of the compound of the formula (I) where Y is the hydrogen atom, when they are applied to the sensitive bacteria. While, the former is more stable and hence more active than the latter against the β-lactamase-producing bacteria.

In the new compound of the formula (I) according to this invention, its 1-oxacephem nucleus is bearing the 3-substituent of the formula —CH$_2$R where R is a heterocyclic group or R is the group —S—Het as defined hereinbefore which may be termed as an S-heterocyclic ring. The heterocyclic group (R) as well as the heterocyclic group (Het) present in the 3-substituent —CH$_2$R may generally be a 5- or 6-membered heterocyclic ring containing 1 to 4 nitrogen atoms as the hetero atom thereof on which heterocyclic ring may further be present one or more substituent such as methyl ethyl, carboxyl, carbamoyl, amino, hydroxyl, carboxymethyl sulfonylmethyl or dimethylaminoethyl group. The heterocyclic ring may further contain 1 or 2 sulfur atoms as the additional, hetero atom thereof. Suitable examples of the heterocyclic group for the group R are the pyridinium residue of the formula

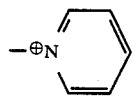

or 4-carbamoylpyridinum residue of the formula

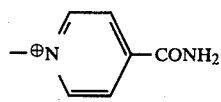

Suitable examples of the heterocyclic group for the symbol Het present in the above-mentioned group —S—Het are: 1-methyl-1H-tetrazole-5-yl of the formula

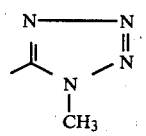

2-carboxymethyl-1H-triazole-5-yl of the formula

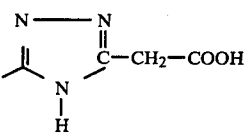

4-methyl-5-oxo-6-hydroxy-4,5-dihydro-1,2,4-triazine-3-yl of the formula

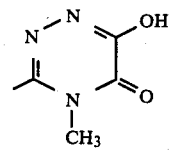

8-substituted or unsubstituted-tetrazole-(1,5-b)-pyridazine-6-yl of the formula

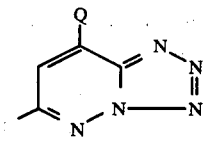

wherein Q is a hydrogen atom or amino, hydroxyl or carboxyl group, 1-sulfonylmethyl-1H-tetrazole-5-yl of the formula

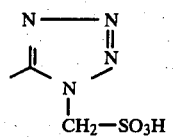

1-sulfonylethyl-1H-tetrazole-5-yl of the formula

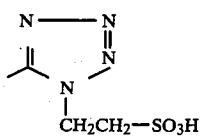

1-carboxymethyl-1H-tetrazole-5-yl of the formula

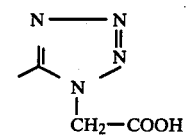

1-methyl-2-carboxy-1H-triazole-5-yl of the formula

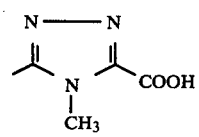

1-dimethylaminoethyl-1H-tetrazole-5-yl of the formula

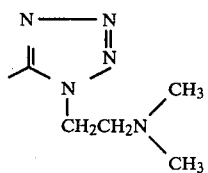

Preferred examples of the 3-substituent —CH₂R are (1-methyl-1H-tetrazole-5-yl) thiomethyl group; (1-carboxylmethyl-1H-tetrazole-5-yl) thiomethyl group; (2-carboxymethyl-1H-tetrazole-5-yl) thiomethyl group; (4-methyl-5-oxo-6-hydroxy-4,5-dihydro-1,2,4-triazine-3-yl) thiomethyl group; (8-amino-tetrazolo-(1,5-b)-pyridazine-6-yl) thiomethyl group; (pyridinium) methyl group; (4-carbamoyl-pyridinium) methyl group; and (1-dimethylaminoethyl-1H-tetrazole-5-yl) thiomethyl group.

According to a preferred embodiment of the first aspect invention, there are provided a new 1-oxadethiacephalosporin derivative of the general formula (I″):

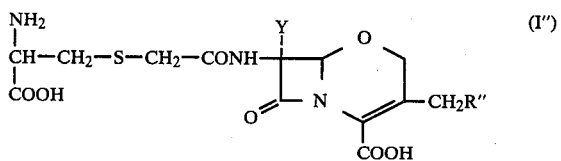

wherein R″ is (1-methyl-1H-tetrazole-5-yl) thio group; (1-carboxylmethyl-1H-tetrazole-5-yl) thio group; (2-carboxymethyl-1H-tetrazole-5-yl) thio group; (4-methyl-5-oxo-6-hydroxy-4,5-dihydro-1,2,4-triazine-3-yl) thio group; (8-amino-tetrazolo-(1,5-b)-pyridazine-6-yl) thio group; pyridinium group; 4-carbamoyl-pyridinium group and (1-dimethylaminoethyl-1H-tetrazole-5-yl) thio group, and Y is a hydrogen atom or a methoxy group, and a pharmaceutically acceptable salt and ester thereof.

According to a further preferred embodiment of the first aspect invention, there are provided a new 1-oxadethiacephalosporin derivative of the general formula (I‴):

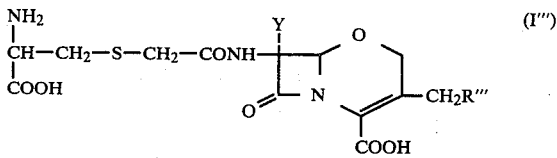

wherein R‴ is (1-methyl-1H-tetrazole-5-yl) thio group or 4-carbamoylpyridinium residue, and Y is a hydrogen atom or a methoxy group, and a pharmaceutically acceptable salt and ester thereof.

As the particular examples of the compound of the general formula (I) according to this invention, the following compounds are mentioned.

(1) 7β-[(2D-2-Amino-2-carboxy)ethylthioacetoamido]-7α-methoxy-3-[(1-methyl-1H-tetrazol-5-yl)thiomethyl]-1-oxadethia-3-cephem-4-carboxylic acid.

(2) 7β-[(3D-3-Amino-3-carboxy)propylthioacetoamido]-7α-methoxy-3-[(1-methyl-1H-tetrazol-5-yl)thiomethyl]-1-oxadethia-3-cephem-4-carboxylic acid.

(3) ∂β-[(2D-2-Amino-2-carboxy)ethylthiopropioamido]-7α-methoxy-3-[(1-methyl-1H-tetrazol-5-yl)thiomethyl]-1-oxadethia-3-cephem-4-carboxylic acid.

(4) 7β-[(2D-2-Amino-2-carboxy)ethylthioacetoamido]-3-[(1-methyl-1H-tetrazol-5-yl)thiomethyl]-1-oxadethia-3-cephem-4-carboxylic acid.

(5) 7β-[(2D-2-Amino-2-carboxy)ethylthioacetoamido]-3-[(4-carbamoylpyridinium)methyl]-1-oxadethia-3-cephem-4-carboxylic acid.

(6) 7β-[(2D-2-Amino-2-carboxy)ethylthioacetoamido]-7α-methoxy-3-[(4-carbamoylpyridinium)methyl]-1-oxadethia-3-cephem-4-carboxylic acid.

(7) 7β-[(3D-3-Amino-3-carboxy)propylthioacetoamido]-7α-methoxy-3-[(4-carbamoylpyridinium)methyl]-1-oxadethia-3-cephem-4-carboxylic acid.

(8) 7β-[(2D-2-Amino-2-carboxy)ethylthiopropioamido]-7α-methoxy-3-[(4-carbamoylpyridinium)methyl]-1-oxadethia-3-cephem-4-carboxylic acid.

(9) 7β-[(2D-2-Amino-2-carboxy)ethylthioacetoamido]-7α-methoxy-3-[(4-methyl-5-oxo-6-hydroxy-4,5-dihydro-1,2,4-triazine-3-yl)thiomethyl]-1-oxadethia-3-cephem-4-carboxylic acid.

(10) 7β-[(2D-2-Amino-2-carboxy)ethylthioacetoamido]-7α-methoxy-3-[(8-amino-tetrazolo-(1,5-b)-pyridazine-6-yl)thiomethyl]-1-oxadethia-3-cephem-4-carboxylic acid.

(11) 7β[(2D-2-amino-2-carboxy)ethylthioacetoamido]-7α-methoxy-3-[(1-dimethylaminoethyl-1H-tetrazole-5-yl)thiomethyl]-1-oxadethia-3-cephem-4-carboxylic acid.

(12) 1-Acetoxyethyl 7β-[(2D-2-amino-2-ethoxycarboxy)ethylthioacetoamido]-7α-methoxy-3-[(1-methyl-1H-tetrazol-5-yl)thiomethyl]-1-oxadethia-3-cephem-4-carboxylate.

(13) 1-Acetoxyethyl 7β-[(2D-2-amino-2-carboxy)ethylthioacetoamido]-7α-methoxy-3-[(1-methyl-1H-tetrazol-5-yl)thiomethyl]-1-oxadethia-3-cephem-4-carboxylate.

(14) 1-Ethoxyethyl 7β-[(2D-2-amino-2-ethoxycarboxy)ethylthioacetoamido]-7α-methoxy-3-[(1-methyl-1H-tetrazol-5-yl)thiomethyl]-1-oxadethia-3-cephem-4-carboxylate.

(15) 7β-[(2D-2-amino-2-ethoxycarboxy)ethylthioacetoamido]-7α-methoxy-3-[(1-methyl-1H-tetrazol-5-yl)thiomethyl]-1-oxadethia-3-cephem-4-carboxylic acid.

(16) 1-Ethoxyethyl 7β-[(2D-2-amino-2-ethoxycarboxy)ethylthioacetoamido]-7α-methoxy-3-[(4-methyl-5-oxo-6-hydroxy-4,5-dihydro-1,2,4-triazine-3-yl)thiomethyl]-1-oxadethia-3-cephem-4-carboxylate.

(17) 1-Acetoxyethyl 7β[(2D-2-amino-2-ethoxycarboxy)ethylthioacetoamido]-7α-methoxy-3-[(1-dimethylaminoethyl-1H-tetrazole-5-yl)thiomethyl]-1-oxadethia-3-cephem-4-carboxylate.

The compound of the formula (I) according to this invention exhibits a high "in vitro" antibacterial activity against bacteria. Table 1 below shows the minimum inhibitory concentrations of the compounds which were prepared in the Examples 1-3 illustrated hereinafter.

TABLE 1

| Test Compounds | Minimum Inhibitory Concentration "in vitro" (μg/ml) | |
| --- | --- | --- |
| | Escherichia coli No. 29 | Escherichia coli GN |
| Ex. 1 Compound | 0.39 | 0.39 |
| Ex. 2 Compound | 0.39 | 3.13 |
| Ex. 3 Compound | 0.78 | 0.78 |

The antibacterial spectrum of the Example 1 Compound, that is, 7β-[(2D-2-amino-2-carboxy) ethylthioacetoamido]-7α-methoxy-3-[(1-methyl-1H-tetrazole-5-yl)thiomethyl]-1-oxadethia-3-cephem-4-carboxylic acid (as the mono-sodium salt) was measured and is shown in Table 2 below. The minimum concentrations of the test compound inhibitory to the growth of various bacteria were determined by preincubating a plate culture of the test microorganism in tripticase soy broth (a product of BBL. Co.) at 37° C. for overnight, diluting the incubated broth to a 100-fold volume with the same soy broth as used in the pre-incubation to give an inoculum, inoculating the inoculum so prepared to a nutrient agar (Difco) as the culture medium for measurement of MIC., and subsequently incubating the inoculated medium at 37° C. for 20 hours. For comparison, the antibacterial spectra of 7β-(α-p-hydroxyphenyl-α-carboxyacetoamido)-7α-methoxy-3-[(1-methyl-1H-tetrazole-5-yl)thiomethyl]-1-oxadethia-3-cephem-4-carboxylic acid (as the di-sodium salt) of U.S. Pat. No. 4,138,486 (abbreviated as "6059-S Compound") and of 7β-[(2D-2-amino-2-carboxy)ethylthioacetoamido]-7α-methoxy-3-[(1-methyl-1H-tetrazole-5-yl)thiomethyl]-3-cephem-4-carboxylic acid (as the mono-sodium salt) of Belgian Pat. No. 880,656 (or copending U.S. Patent Application Ser. No. 104,220) (abbreviated as "MT-141 Compound") were determined in the same manner as above and are shown in Table 2 below.

TABLE 2

| Test Organisms | MIC. (mcg./ml) | | |
| --- | --- | --- | --- |
| | Example 1 Compound of this invention | 6059-S Compound (Comparative) | MT-141 Compound (Comparative |
| Sta. aureus 209P JC-1 | 3.13 | 6.25 | 12.5 |
| Sta. aureus Smith (I) | 1.56 | 6.25 | 6.25 |
| B. subtilis ATCC 6633 | 1.56 | 25 | 6.25 |
| E. coli W 3630 RGN 823 | ≦ 0.025 | 0.05 | 0.05 |
| E. coli W 3630 RGN 238 | 0.39 | 0.20 | 0.78 |
| E. coli ML 1410 | 0.39 | 0.10 | 0.78 |
| Kleb. pneumoniae GN 69 | 0.78 | 0.39 | 1.56 |
| Pro. mirabilis GN 79 | 0.20 | 0.39 | 0.39 |
| Sal. typhimurium LT-2 | 0.39 | 0.20 | 0.78 |
| Shigella dysenteriae Shigae | 0.20 | 0.10 | 0.39 |
| Pro. vulgaris GN 76 | 0.39 | 0.39 | 0.39 |
| Pro. morganii 1510 | 0.78 | 0.39 | 0.78 |
| Citro freundii GN 346/16 | 0.78 | 0.10 | 0.78 |
| Ps. aeruginosa MB-3829 | 12.5 | 3.13 | 12.5 |
| Ps. cepacia M-0527 | 3.13 | 6.25 | 6.25 |

All of the new compounds of the general formula (I) according to this invention have a low toxicity, as demonstrated by that they all exhibit an $LD_{50}$ value of 7~8 g/kg upon intravenous injection in mice for estimation of their acute toxicity. Therefore, the new compounds of this invention are useful in therapeutic treatment of infections by various gram-negative and gram-positive bacteria, including the resistant bacterial strains. The new compounds of this invention as well as their pharmaceutically acceptable salt and ester may be administered orally, intraperitoneally, intravenously, subcutaneously or intramuscularly using any pharmaceutical form known to the art for such administration and in a similar manner to the known cephalosporins. For instance, the new compounds of this invention may be administered orally using any pharmaceutical form known to the art for oral administration. Examples of the pharmaceutical forms for oral administration are powders, capsules, tablets, syrup and the like. The new compounds of this invention may be administered by intramuscular or intravenous or subcutaneous injection or drip infusion at a dosage of 0.5 to 2.0 g per person two to three times per day. A suitable dose of the new compounds of this invention for effective treatment of bacterial infections is in a range of 2 to 4 g per person a day when it given orally. It is preferred that said dose should be orally administered in three to four aliquots per day. Moreover, the new compounds of this invention may be formulated into a suppository which contains the active compound at a concentration of 0.5~15% by weight in mixture with a known suppository base. Furthermore, the new compounds of this invention are useful for sterilization of surgical instruments.

According to a third aspect of this invention, therefore, there is provided an antibacterial composition comprising an antibacterially effective amount of the new compound of the aforesaid formula (I) or the pharmaceutically acceptable salt thereof or the pharmaceutically acceptable ester thereof, as the active ingredient, in combination with a pharmaceutically acceptable carrier for the active ingredient. In the pharmaceutical composition of this invention, the active ingredient compound may be incorporated therein in an amount of 0.1% to 90% by weight of the whole composition.

According to another aspect of this invention, there is provided a method for inhibiting bacterial growth which comprises administering an antibacterially effective and safe amount of a new compound of this invention according to the aforesaid formula (I) to an animal, including men, susceptible to the bacterial growth. There is further provided a method for inhibiting in vitro bacterial growth, which comprises contacting a surface susceptible to said bacterial growth, with an antibacterially effective amount of a compound of this invention.

The new compound of this invention according to the aforesaid formula (I) is advantageous in that it exhibits a high antibacterial activity in vivo and shows a high curative effect in the chemotherapeutic treatment of animals, including men, which have been infested by bacteria. In order to demonstrate this, the test for therapeutically treating the bacterial infection in mice was conducted by inoculating an inoculum of Escherichia coli No. 29 (as a bacteria suspension in water containing 2.5% mucin) intraperitoneally into mice groups (each group consisting of five male mice of ICR-strain, 4-week-aged, 20 g average body weight) at an inoculum size of $2.0 \times 10^7$ cells per mouse. Thirty minutes after the inoculation, the mice were each treated by subcutaneous injection of 0.2 ml of a solution of the test compound in physiological saline. In this way, the $ED_{50}$ value of the test compounds was determined. Cefoxitin and the 6059-S Compound (di-Na salt) were also tested in the same manner as above, for the comparison purpose. The test results are shown in Table 3 below.

TABLE 3

| Test Compounds | ED$_{50}$ value (mg/mouse) |
| --- | --- |
| Example 1 Compound | 0.03 |
| Example 2 Compound | 0.05 |
| Cefoxitin (Comparative) | 0.50 |
| 6059-S Compound (Comparative) | 0.16 |

From the above Table, it is clear that the new compound of this invention exhibit a higher curative effect, as compared to cefoxithin and 6059-S compound which are known to be useful antibacterial agent in chemotherapeutic treatment of various bacterial infections.

The new compound of this invention according to the aforesaid formula (I) may be produced via various routes principally starting from a 7-amino-1-oxadethiacephem compound of the formula (IV):

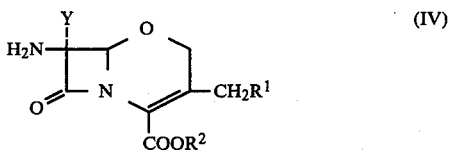
(IV)

wherein Y is a hydrogen atom or a methoxy group, $R^1$ is a heterocyclic group or a group —S—Het as defined hereinbefore, and $R^2$ is a hydrogen atom or a known carboxyl-protecting group. The preparation of this starting compound (IV) may be achieved in a known manner as described, for example, in the "Canadian Journal of Chemistry" 50, 2894 (1972); "Journal of American Chemical Society" 96, 7582 (1977); "Journal of Medicinal Chemistry" 20, 551(1977); "Journal of Medicinal Chemistry" 22, p. 757 (1979); and "Journal of American Chemical Society" 101, 4403 (1979).

Basically and conveniently, the preparation of the starting compound (IV) may be made by a method comprising heating a compound of the formula (V)

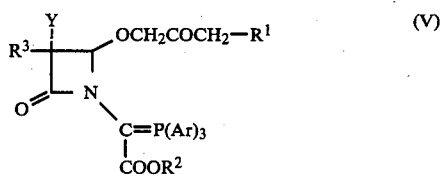
(V)

wherein Y, $R^1$ and $R^2$ are as defined above for the formula (IV), and $R^3$ is an acylamino group and Ar is an aryl group such as phenyl, in an inert organic solvent such as aromatic hydrocarbon, halohydrocarbon and dioxane at a temperature of 70°~150° C. for several hours for cyclisation of the compound (V), and then treating the resulting cyclization product with phosphorous pentachloride and an organic base such as pyridine and N,N-di-methylaniline at a temperature of −20° to 40° C. for preferential conversion of the 7-acylamino group ($R_3$) into the free 7-amino group. The initial compound of the above formula (V), in turn, may be prepared by various known methods as described, for example, in U.S. Pat. No. 4,180,571.

To produce the compound of this invention according to the formula (I), for instance, it is possible to follow a first route in which the 7-amino-1-oxadethiacephem compound of the formula (IV) is reacted with a haloalkanoic acid or its reactive derivative of the formula (VI)

$$Z-(CH_2)_yCOX \quad (VI)$$

wherein Z is a halogen atom, particularly bromine or chlorine, X is —OH or a bromo or chloro group or other reactive group functionally equivalent to the radical —OH present in the carboxyl group, and y is an integer of 1~3, to produce the condensation product of the formula (II')

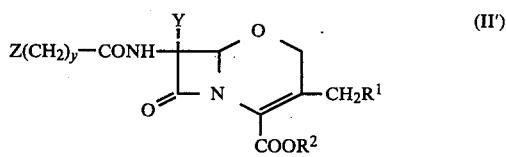
(II')

wherein $R^1$, $R^2$, Y, Z and y are as defined above, which is then reacted with the amino acid compound of the formula (III)

(III)

wherein x is an integer of 1 to 3, and, if necessary followed by removing the carboxyl-protecting group ($R^2$) when present.

Alternatively, it is also possible to take a second route in which the 7-amino-1-oxadethia-cephem compound of the formula (IV) is reacted with a compound of the formula (VII)

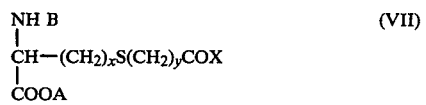
(VII)

wherein X is a group —OH or a bromo or chloro group or other reactive group functionally equivalent to the group —OH present in the carboxyl group, x and y are each an integer of 1~3, A is a known carboxyl-protecting group, and B is a known amino-protecting group, followed by removing the residual protective groups (A,B) from the resulting condensation product. The reagent of the formula (VI) as well as the reagent of the formula (VII) which are employed in the above-mentioned two routes, respectively, are possible to be in the form of the active derivative of a carboxylic acid which may be an acid halide, mixed acid anhydride, succinylimino derivative or p-nitrophenyl ester. With respect to the formula (VII), the amino-protecting group (B) may include t-butoxycarbonyl, trichloroethoxycarbonyl and substituted or unsubstituted benzyloxycarbonyl groups. The carboxyl-protecting group (A) may include diphenylmethyl, trichloroethyl, substituted or unsubstituted benzyl and t-butyl groups. These protecting groups all can be introduced and removed according to a conventional protecting or de-protecting technique. The halogen atom (Z) in the formula (II') or (VI) may be chlorine, bromine or iodine, but chlorine and bromine are suitable.

In the first or second route mentioned above, the reaction of the 7-amino-1-dethiaoxa-cephem compound of the formula (IV) with the haloalkanoic acid compound of the formula (VI) or with the compound of the formula (VII) may usually be conducted in an inert organic solvent under such reaction conditions for the formation of amido linkage which are known in conventional synthesis of peptides. The solvent for this purpose may be an organic solvent such as dichloromethane, chloroform, ethyl acetate, dimethylformamide and the like. When the reagent compound of the formula (VI) or (VII) is used in the form of the acid halide as one of the reactive acid derivatives, the reaction of it with the compound of the formula (IV) may be carried out at a temperature of from ambient temperature to a lower temperature than 0° C. in the presence of an acid-binding agent which may be a known trimethylsilylating agent or a organic base, for example, a tertiary amine such as tri-alkylamine, pyridine, dimethylaniline, and the like. While, when the reagent compound of the formula (VI) or (VII) is used in the form of the free carboxylic acid, the reaction may conveniently be carried out according to a known active ester method in the presence of a dehydrating agent such as N,N-dicyclohexylcarbodiimide. The time required for the reaction may vary depending on the reactivity of the carboxylic acid derivative of the formula (VI) or (VII) employed and may usually be in a range of 1 to 5 hours.

In the above-mentioned first route for producing the compound of the formula (I), the reaction of the 7-amino compound of the formula (IV) with the haloalkanoic acid reagent of the formula (VI) is followed by a subsequent reaction of the resultant condensation product of the formula (II') with the amino acid compound of the formula (III). This subsequent reaction may proceed at ambient temperature or at a lower temperature in an inert solvent, preferably in the presence of an alkali metal (hydrogen) carbonate, a tri-alkylamine, pyridine or the like as the acid-binding agent. This subsequent reaction can be completed usually in 1 to 5 hours, although in general the required reaction time may vary mainly depending on the reactivity of the halo group (Z) present in the compound (II'), the nature of the acid-binding agent and the solvent used.

The process of the second aspect invention now claimed is corresponding to a part, that is, the later phase of the first route as described in the above.

In carrying out the process of the second aspect invention, the 1-oxacephem compound of the formula (II) is reacted with an equimolar or substantially equimolar proportion of the sulfur-containing amino acid of the formula (III) in a liquid reaction medium which may be water, an aqueous alkanol such as aqueous methanol in which the reactants can be dissolved or suspended. The reaction temperature may be in a range of 0° to 30° C. although the reaction may conveniently be conducted at ambient temperature. As the hydrogen halide is liberated during the condensation, it is preferred to effect the condensation in the presence of an acid-binding agent such as an alkali or organic base.

D-cysteine is a preferred example of the amino acid reactant of the formula (III).

The amino acid reactant of the formula (III) may, if desired, be in the form of its functionally equivalent derivative, for example, in the form of an alkali metal mercaptide at the terminal thiol group thereof.

When the 1-oxacephem compound of the formula (II) is used in the form of its carboxyl-protected derivative where the group R' is a known carboxyl-protecting group such as an ester-forming group, for example, an alkyl or aryl group, the condensation product of the formula (I') as formed may, if necessary or desired, be subjected to a deprotecting step for removal of the carboxyl-protecting group (R') which may be conducted in a known manner. When the carboxyl-protecting group (R') is an alkyl or aryl group, the removal of this ester-forming group may be achieved by acidic or alkaline hydrolysis in a known manner. If the ester-forming group as the group R' is a pharmaceutically acceptable one, it is not necessary to effect the removal of such ester-forming group from the condensation product of the formula (I').

When the condensation product of the formula (I) or (I') is obtained in the form of the free carboxylic acid or in the form of a carboxylic acid ester, it may further be converted into its pharmaceutically acceptable salt by reacting with a pharmaceutically acceptable base such as an alkali metal carbonate or hydroxide according to a known method for the formation of the carboxylate (salt).

The desired product of the formula (I) obtained as above, either in the free carboxylic acid form or in the pharmaceutically acceptable carboxylate form, may be recovered from the reaction mixture by a conventional procedure. For example, the reaction mixture containing the desired product (I) may be diluted with water and then treated with an adsorptive resin or activated carbon for adsorption of the desired product, followed by elution with water or with an aqueous organic solvent such as aqueous ethanol, so that the final desired product is isolated and purified. If necessary, further isolation and purification may be achieved by column chromatography on a gel-filtration agent such as Sephadex LH-20 or G-10 (a product of Pharmacia Co., Sweden) or a microporous nonionic adsorbent resin such as a styrene-divinylbenzene copolymer, for example, Diaion HP-20 (a product of Mitsubishi Kasei Co., Japan).

This invention is now illustrated with reference to the following Examples to which this invention is not limited in any way.

EXAMPLE 1

(a) 7β-Amino-7α-methoxy-3-[(1-methyl-1H-tetrazol-5-yl)thiomethyl]-1-oxadethia-3-cephem-4-carboxylic acid benzyl ester (150 mg) was dissolved in a mixture of ethyl acetate (7 ml) and bis(trimethyl-silyl) acetoamide (370 mg). To the solution was added a solution of bromoacetyl bromide (120 mg) in ethyl acetate (2 ml), followed by stirring the admixture at −20° C. for 1 hour and at 0° to 5° C. for further 1 hour. Ethyl acetate (10 ml) was added to the resulting reaction solution, and the mixture was washed with 5% aqueous hydrochloric acid (10 ml), with water (10 ml), with 5% aqueous sodium hydrogen carbonate (10 ml) and finally with water (10 ml). The ethyl acetate phase was separated from the aqueous phase and then dried over anhydrous magnesium sulfate and concentrated to dryness under reduced pressure to give 220 mg of an oily product.

The oily product obtained as above was taken up into dry methylene chloride (10 ml), and the resulting solution was mixed with anisole (440 mg) and a solution of aluminium trichloride (266 mg) in nitromethane (4 ml) under stirring and ice-cooling. The admixture was stirred under ice-cooling for 15 minutes and then at ambient temperature for further 1.5 hours. The reaction solution, after addition of 60 ml of ethyl acetate thereto, was washed twice with 2% aqueous hydrochloric acid and then extracted twice with 5% aqueous sodium hydrogen carbonate. After addition of ethyl acetate (40 ml), the extract was adjusted to pH 1 by addition of 5% aqueous hydrochloric acid. The ethyl acetate phase was separated from the aqueous phase, and the remaining aqueous phase was further extracted with 30 ml of ethyl acetate. The extracts (the solution in ethyl acetate) were combined together, dried over anhydrous magnesium sulfate and then concentrated to dryness to give 40 mg of 7β-(2-bromoacetoamido)-7α-methoxy-3-[(1-methyl-1H-tetrazol-5-yl)thiomethyl]-1-oxadethia-3-cephem-4-carboxylic acid.

(b) The product (40 mg) obtained in the above procedure was suspended in water (10 ml), and the suspension was adjusted to pH 7 by addition of aqueous sodium hydrogen carbonate, so that the aforesaid cephem compound was dissolved in water. D-Cysteine (20 mg) was then added to the resultant solution, and the reaction was effected at room temperature for 1.5 hours while the pH of the reaction solution was kept at 7~7.5. After completion of the reaction, the reaction solution was adjusted to pH 5.5 to 6.5 by addition of hydrochloric acid and concentrated. The concentrated solution was passed through a column of 40 ml of an adsorbent resin, Diaion HP-20 ( a product of Mitsubishi Kasei Co., Japan), which was then eluted with water. Fractions of the eluate containing the desired compound were collected, concentrated under reduced pressure and freeze-dried to afford 45 mg of 7β-[(2D-2-amino-2-carboxy)ethylthioacetoamido]-7α-methoxy-3-[(1-methyl-1H-tetrazol-5-yl)thiomethyl]-1-oxadethia-3-cephem-4-carboxylic acid sodium salt as a colorless powder.

Melting point: 129° to 135° C. (Decomp.).

This product showed an Rf 0.35 in a silica gel thin layer chromatography (developed with n-butanolacetic acid-water=2:1:1)

Elemental Analysis: Calculated for $C_{16}H_{20}N_7O_8S_2$·Na·2H$_2$O (561.53): C 34.22, H 4.31, N 17.46%. Found: C 33.91, H 4.41, N 16.96%.

PMR.(80 Hz) (in deutero-water): δ3.36 s(2H), 3.41 s(3H), 3.93 s(3H), 4.05 q(2H), 4.46 s(2H), 5.05 s(1H).

EXAMPLE 2

The process of Example 1 was repeated using 150 mg of 7β-amino-3-[(1-methyl-1H-tetrazol-5-yl)thiomethyl]-1-oxadethia-3-cephem-4-carboxylic acid benzyl ester. 7β-[(2D-2-Amino-2-carboxy)ethylthioacetoamido]-3-[(1-methyl-1H-tetrazol-5-yl)thiomethyl]-1-oxadethia-3-cephem-4-carboxylic acid sodium salt was obtained in a yield of 50 mg.

m.p.: 133°~138° C. (Decomp.).

This product showed an Rf 0.39 in a silica gel thin layer chromatography (developed with n-butanolacetic acid-water=2:1:1).

EXAMPLE 3

The process of Example 1 was repeated using 300 mg of 7β-amino-7α-methoxy-3-[(4-carbamoyl-pyridinium)-methyl]-1-oxadethia-3-cephem-4-carboxylic acid benzyl ester. 7β-[(2D-2-Amino-2-carboxy)ethylthioacetoamido]-7α-methoxy-3-[(4-carbamoylpyridinium)methyl]-1-oxadethia-3-cephem-4-carboxylic acid was afforded in a yield of 65 mg.

m.p.: 115°~120° C. (Dec.)

This product showed an Rf 0.21 in a silica gel thin layer chromatography (developed with n-butanol-acetic acid-water=2:1:1).

Elemental Analysis: Calculated for $C_{20}H_{24}N_5O_9S$·H$_2$O (528.53): C 45.45, H 4.96, N 13.25%. Found: C 45.42, H 5.05, N 13.15%.

EXAMPLE 4

(a) 7β-Amino-7α-methoxy-3-[(1-methyl-1H-tetrazol-5-yl)thiomethyl]-1-oxadethia-3-cephem-4-carboxylic acid benzhydryl ester (150 mg) was dissolved in dichloromethane (5 ml). To the resulting solution were added dimethylaniline (0.042 ml) and bromoacetyl bromide (70 mg) at 31 10° C., and the admixture obtained was stirred at −10° C. for 1.5 hours. The reaction solution was washed with aqueous hydrochloric acid of pH 2, with 5% aqueous sodium carbonate and finally with water, and further dried over anhydrous sodium sulfate and concentrated to dryness under reduced pressure to give 190 mg of 7β-(2-bromoacetoamido)-7α-methoxy-3-[(1-methyl-1H-tetrazol-5-yl)thiomethyl]-1-oxadethia-3-cephem-4-carboxylic acid benzhydryl ester as hygroscopic powder.

The powdery product obtained as above was dissolved in anisole (0.5 ml), and trifluoroacetic acid (1 ml) was added to the resulting solution at −10° C., followed by stirring for 1 hour at −10° C. to effect the removal of the benzhydryl group. The reaction solution was concentrated to dryness under reduced pressure below 30° C. The residue thus obtained was taken up into ethyl acetate (20 ml), washed with water, and then extracted with an aqueous sodium hydrogen carbonate of pH 8 (20 ml). The aqueous extract was adjusted to pH 1.0 with 5 N aqueous hydrochloric acid and then extracted with two 20 ml portions of ethyl acetate. The ethyl acetate phases (the extracts) were combined together, washed with water, dried over anhydrous magnesium sulfate and evaporated to dryness under reduced pressure to obtain 98 mg of 7β-(2-bromoacetoamido)-7α-methoxy-3-[(1-methyl-1H-tetrazol-5-yl)thiomethyl]-1-oxadethia-3-cephem-4-carboxylic acid.

(b) The product (98 mg) obtained in the above procedure was suspended in 5 ml of water, and the suspension was adjusted to pH 7.0 with a 5% aqueous sodium hydrogen carbonate to effect the dissolution of the cephem compound. D-Cysteine (45 mg) was added to the solution obtained, and the mixture was stirred at 5° to 10° C. for 1 hour, while the mixture was maintained at a pH of 6.8 to 7.0 by addition of the aqueous sodium hydrogen carbonate. The reaction solution was adjusted to pH 5.0 with 5 N aqueous hydrochloric acid. The reaction solution was concentrated to a volume of about 2 ml. The concentrated solution was placed in a column of 50 ml of an adsorbent resin, Amberlite XAD-2 (a product of Rohm & Haas Co., U.S.A.) and the column was developed with water. The fractions of the eluate which contained the desired product were collected, concentrated under reduced pressure and freeze-dried to give 73 mg of 7β-[(2D-2-amino-2-carboxy)ethylthioacetoamido]-7α-methoxy-3-[(1-methyl-1H-tetrazol-5-yl)thiomethyl]-1-oxadethia-3-cephem-4-carboxylic acid sodium salt as a colorless powder of m.p. 129°~135° C. (Dec.).

EXAMPLE 5

7β-(2-Bromoacetoamido)-7α-methoxy-3-[(1-dimethylaminoethyl-1H-tetrazole-5-yl)thiomethyl]-1-oxadethia-3-cephem-4-carboxylic acid (100 mg) was suspended in water (4 ml), and the suspension obtained was adjusted to pH 6.8 by addition of 10% aqueous sodium hydrogen carbonate, so that the aforesaid cephem compound was dissolved in water. The solution so obtained was then admixed with D-cysteine hydrochloride (50 mg), followed by stirring at 0°~5° C. for 2 hours while the reaction solution was maintained at pH 6.8~7.0. The reaction solution was then adjusted to pH 6 by addition of 5 N hydrochloric acid and concentrated to a volume of about 5 ml. The concentrated solution was passed through a column of 60 ml of a microporous, non-ionic adsorbent resin, Diaion HP-20, which was then eluted with water. Fractions of the eluate containing the desired compound were collected, concentrated under reduced pressure and freeze-dried to afford 98 mg of a colorless powder of 7β-(2D-2-amino-2-carboxy)ethylthioacetoamido]-7α-methoxy-3-[(1-dimethylaminoethyl-1H-tetrazole-5-yl)thiomethyl]-1-oxadethia-3-cephem-4-carboxylic acid.

This product showed an Rf 0.32 in a silica gel thin layer chromatography (developed with n-butanol-acetic acid-water=2:1:1).

EXAMPLE 6

7β-(2-Bromoacetoamido)-7α-methoxy-3-[(1-methyl-1H-tetrazole-5-yl)thiomethyl]-1-oxadethia-3-cephem-4-carboxylic acid (50 mg) was suspended in water (5 ml), and the suspension obtained was adjusted to pH 7.0 by addition of 5% aqueous sodium hydrogen carbonate, so that the aforesaid cephem compound was dissolved in water. The solution so obtained was admixed with D-cysteine ethyl ester hydrochloride (18 mg), followed by stirring at 5°~10° C. for 3 hours while the reaction solution was maintained at pH 6.8~7.0. The reaction solution was then adjusted to pH 6 by addition of 5 N hydrochloric acid and subsequently passed through a column of 30 ml of Diaion HP-20 resin, which was subsequently washed with water and eluted with 30% aqueous ethanol. The fractions of the eluate containing the desired product were collected, concentrated under reduced pressure and freeze-dried to yield 41 mg of a colorless powder of 7β-[(2D-2-amino-2-ethoxycarbonyl)ethylthioacetoamido]-7α-methoxy-3-[(1-methyl-1H-tetrazole-5-yl)thiomethyl]-1-oxadethia-3-cephem-4-carboxylic acid.

This product showed an Rf 0.57 in a silica gel thin layer chromatography (developed with acetone-methanol=2:1).

EXAMPLE 7

7β-(2-Bromoacetoamido)-7α-methoxy-3-[(4-methyl-5-oxo-6-hydroxy-4,5-dihydro-1,2,4-triazine-3-yl)thiomethyl]-1-oxadethia-3-cephem-4-carboxylic acid (60 mg) was suspended in water (3 ml), and the suspension obtained was adjusted to pH 7 by addition of 5% aqueous sodium hydrogen carbonate, so that the cephem compound was dissolved in water. The solution so obtained was admixed with D-cysteine hydrochloride (28 mg), followed by stirring for 2 hours while the reaction solution was maintained at pH 6.8~7.0. The reaction solution was further processed in the same manner as in Example 5 to give 52 mg of a colorless powder of sodium 7β-[(2D-2-amino-2-carboxy)ethylthioacetoamido[-7α-methoxy-3-[(4-methyl-5-oxo-6-hydroxy-4,5-dihydro-1,2,4-triazine-3-yl)thiomethyl]-1-oxadethia-3-cephem-4-carboxylate. This product showed an Rf 0.38 in a silica gel thin layer chromatography (developed with n-butanol-acetic acid-water=2:1:1).

EXAMPLE 8

(a) 7β-(2-Bromoacetoamido)-7α-methoxy-3-[(1-methyl-1H-tetrazole-5-yl)thiomethyl]-1-oxadethia-3-cephem-4-carboxylic acid (100 mg) was dissolved in N,N-dimethylformamide (1 ml), and to the resultant solution were added 0.03 ml of triethylamine at −25° C. and then dropwise added 0.5 ml of a solution of 55 mg of 1-acetoxyethyl iodide in N,N-dimethylformamide over 10 minutes, followed by stirring at −5° C. to 0° C. for 1 hour. The reaction solution was diluted with water (5 ml) and then extracted with 20 ml of ethyl acetate. The extract in ethyl acetate was washed twice with 5 ml portions of water, dried over anhydrous sodium sulfate and concentrated to dryness under reduced pressure. The residue was washed with petroleum ether to afford 120 mg of 1-acetoxyethyl 7β-(2-bromoacetoamido)-7α-methoxy-3-[(1-methyl-1H-tetrazole-5-yl)thiomethyl]-oxadethia-3-cephem-4-carboxylate.

(b) The product obtained as above was dissolved in 2 ml of acetone, and the resulting solution was admixed with 5 ml of water and then with 20 mg of D-cysteine methyl ester hydrochloride, followed by stirring at 0°~5° C. for 3 hours while the reaction solution was kept at pH 6.5 by addition of 5% aqueous sodium hydrogen carbonate. The reaction solution was adjusted to pH 8.0 by addition of the aqueous sodium hydrogen carbonate and then extracted with 20 ml of ethyl acetate. The extract in ethyl acetate was concentrated to a volume of 2 ml, and the concentrated solution was passed through a column of 40 ml of Sephadex LH-20 which had been saturated with ethyl acetate. The column was developed with ethyl acetate, and the fractions of the eluate containing the desired product were collected and concentrated to dryness under reduced pressure to afford 95 mg of a colorless powder of 1-acetoxyethyl 7β-[(2D-2-amino-2-methoxycarbonyl)ethylthioacetoamido]-7α-methoxy-3-[(1-methyl-1H-tetrazole-5-yl)thiomethyl]-1-oxadethia-3-cephem-4-carboxylate.

This product showed an Rf 0.73 in a silica gel thin layer chromatography (developed with ethyl acetate acetone=5:1).

What we claim is:

1. A 1-oxadethiacephalosporin of the formula (I):

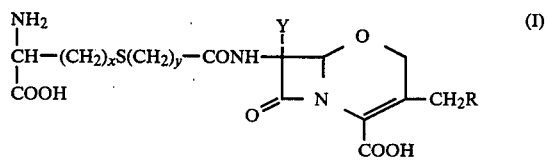

wherein R is (1-methyl-1H-tetrazole-5-yl)thio group; (1-carboxylmethyl-1H-tetrazole-5-yl)thio group; (2-carboxymethyl-1H-tetrazole-5-yl)thio group; (4-methyl-5-oxo-6-hydroxy-4,5-dihydro-1,2,4-triazine-3-yl)thio group; (8-amino-tetrazolo-(1,5-b)-pyridazine-6-yl)thio group; pyridinium group; 4-carbamoylpyridinium group, or (1-dimethylaminoethyl-1H-tetrazole-5-yl)thio group, Y is a hydrogen atom or a methoxy group, and x and y each denote an integer of 1, 2 or 3, and pharmaceutically acceptable salt and ester thereof.

2. A 1-oxadethiacephalosporin of the formula (I'''):

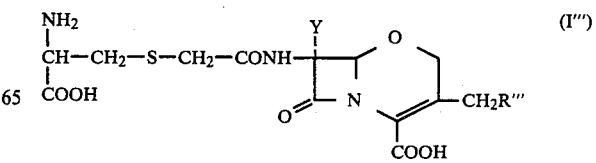

wherein R''' is (1-methyl-1H-tetrazole-5-yl)thio group or 4-carbamoylpyridinium residue, and Y is a hydrogen atom or a methoxy group, and a pharmaceutically acceptable salt and ester thereof.

3. 7β-[(2D-2-Amino-2-carboxy)ethylthioacetoamido]-7α-methoxy-3-[(1-methyl-1H-tetrazole-5-yl)thiomethyl]-1-oxadethia-3-cephem-4-carboxylic acid, and its pharmaceutically acceptable salt and ester.

4. 7β-[(2D-2-Amino-2-carboxy)ethylthioacetoamido]-3-[(1-methyl-1H-tetrazole-5-yl)thiomethyl]-1-oxadethia-3-cephem-4-carboxylic acid, and its pharmaceutically acceptable salt and ester.

5. 7β-[(2D-2-Amino-2-carboxy)ethylthioacetoamido]-3-[(4-carbamoylpyridinium)methyl]-1-oxadethia-3-cephem-4-carboxylic acid, and its pharmaceutically acceptable salt and ester.

6. 7β-[(2D-2-Amino-2-carboxy)ethylthioacetoamido]-7α-methoxy-3-[(1-dimethylaminoethyl-1H-tetrazol-5-yl)thiomethyl]-1-oxadethia-3-cephem-4-carboxylic acid, and its pharmaceutically acceptable salt and ester.

7. The compound according to claim 1, which is selected from 7β-[(3D-3-amino-3-carboxy)propylthioacetoamido]-7α-methoxy-3-[(1-methyl-1H-tetrazol-5-yl)thiomethyl]-1-oxadethia-3-cephem-4-carboxylic acid; 7β-[(2D-2-amino-2-carboxy)ethylthiopropioamido]-7α-methoxy-3-[(1-methyl-1H-tetrazol-5-yl)thiomethyl]-1-oxadethia-3-cephem-4-carboxylic acid; 7β-[(2D-2-amino-2-carboxy)ethylthio-acetoamido]-7α-methoxy-3-[(4-carbamoylpyridinium)methyl]-1-oxadethia-3-cephem-4-carboxylic acid; 7β-[(3D-3-amino-3-carboxy)propylthioacetoamido]-7α-methoxy-3-[(4-carbamoylpyridinium)methyl]-1-oxadethia-3-cephem-4-carboxylic acid; 7β-[(2D-2-amino-2-carboxy)ethylthiopropioamido]-7α-methoxy-3-[(4-carbamoylpyridinium)methyl]-1-oxadethia-3-cephem-4-carboxylic acid; 7β-[(2D-2-amino-2-carboxy)ethylthioacetoamido]-7α-methoxy-3-[(4-methyl-5-oxo-6-hydroxy-4,5-dihydro-1,2,4-triazine-3-yl)thiomethyl]-1-oxadethia-3-cephem-4-carboxylic acid; 7β-[(2D-2-amino-2-carboxy)ethylthioacetoamido]-7α-methoxy-3-[(8-amino-tetrazolo-(1,5-b)-pyridazine-6-yl)thiomethyl]-1-oxadethia-3-cephem-4-carboxylic acid; 1-acetoxyethyl 7β-[(2D-2-amino-2-ethoxy-carboxy)ethylthioacetoamido]-7α-methoxy-3-[(1-methyl-1H-tetrazol-5-yl)thiomethyl]-1-oxadethia-3-cephem-4-carboxylate; 1-acetoxyethyl 7β-[(3D-3-amino-3-carboxy)ethylthioacetoamido]-7α-methoxy-3-[(1-methyl-1H-tetrazol-5-yl)thiomethyl]-1-oxadethia-3-cephem-4-carboxylate; 1-ethoxyethyl 7β-[(2D-2-amino-2-ethoxycarboxy)ethylthioacetoamido]-7α-methoxy-3-[(1-methyl-1H-tetrazol-5-yl)thiomethyl]-1-oxadethia-3-cephem-4-carboxylate; 7β-[(2D-2-amino-2-ethoxycarboxy)-ethylthioacetoamido]-7α-methoxy-3-[(1-methyl-1H-tetrazol-5-yl)thiomethyl]-1-oxadethia-3-cephem-4-carboxylic acid; 1-ethoxyethyl 7β-[(2D-2-amino-2-ethoxycarboxy)ethylthioacetoamido]-7α-methoxy-3-[(4-methyl-5-oxo-6-hydroxy-4,5-dihydro-1,2,4-triazine-3-yl)thiomethyl]-1-oxadethia-3-cephem-4-carboxylate; and 1-acetoxyethyl 7β-[(2D-2-amino-2-ethoxycarboxy)ethylthioacetoamido]-7α-methoxy-3-[(1-dimethylaminoethyl-1H-tetrazole-5-yl)thiomethyl]-1-oxadethia-3-cephem-4-carboxylate.

8. An antibacterial composition comprising an antibacterially effective amount of the 1-oxadethiacephalosporin of claim 1 or its pharmaceutically acceptable salt or ester as the active ingredient, in combination with a pharmaceutically acceptable carrier for the active ingredient.

9. A method fo inhibiting bacterial growth, which comprises administering an antibacterially effective and safe amount of the 1-oxadethiacephalosporin of claim 1 or its pharmaceutically acceptable salt or ester to an animal, including men, susceptible to the bacterial growth.

10. A method for inhibiting in vitro bacterial growth, which comprises contacting a surface susceptible to said bacterial growth, with an antibacterially effective amount of the 1-oxadethiacephalosporin of claim 1 or its pharmaceutically acceptable salt or ester.

* * * * *